(12) United States Patent
Syeda-Mahmood et al.

(10) Patent No.: US 7,783,342 B2
(45) Date of Patent: Aug. 24, 2010

(54) SYSTEM AND METHOD FOR INFERRING DISEASE SIMILARITY BY SHAPE MATCHING OF ECG TIME SERIES

(75) Inventors: Tanveer F. Syeda-Mahmood, Cupertino, CA (US); Fei Wang, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/106,514

(22) Filed: Apr. 21, 2008

(65) Prior Publication Data

US 2010/0081953 A1 Apr. 1, 2010

(51) Int. Cl.
*A61B 5/0432* (2006.01)
(52) U.S. Cl. .................... 600/523; 128/923
(58) Field of Classification Search ......... 600/508–510, 600/513, 515–518, 523, 525; 128/920, 923, 128/925
See application file for complete search history.

(56) References Cited

U.S. PATENT DOCUMENTS

| | | | | |
|---|---|---|---|---|
| 4,589,420 | A * | 5/1986 | Adams et al. | 600/515 |
| 4,974,598 | A * | 12/1990 | John | 600/509 |
| 5,090,418 | A * | 2/1992 | Squires et al. | 600/515 |
| 5,092,343 | A * | 3/1992 | Spitzer et al. | 600/515 |
| 5,311,867 | A * | 5/1994 | Kynor | 600/409 |
| 5,542,429 | A * | 8/1996 | Feng | 600/515 |
| 5,794,624 | A * | 8/1998 | Kwong | 600/515 |
| 5,817,027 | A | 10/1998 | Arand et al. | |
| 6,438,410 | B2 * | 8/2002 | Hsu et al. | 600/516 |
| 6,491,629 | B1 * | 12/2002 | Bousseljot et al. | 600/300 |
| 6,709,399 | B1 | 3/2004 | Shen et al. | |
| 2005/0033191 | A1 * | 2/2005 | Povinelli et al. | 600/515 |
| 2005/0222508 | A1 * | 10/2005 | Moreno et al. | 600/509 |
| 2006/0129052 | A1 * | 6/2006 | Drakulic | 600/509 |

OTHER PUBLICATIONS

Syeda-Mahmood, et al. "Shape-based Matching of ECG Recordings" Proceedings of the 29th Annual International Conference of the IEEE EMBS. Aug. 23-26, 2007, pp. 2012-2018.*

(Continued)

*Primary Examiner*—Kennedy J Schaetzle
*Assistant Examiner*—Jessica Sarcione
(74) *Attorney, Agent, or Firm*—Cantor Colburn LLP; Van Nguy

(57) ABSTRACT

A method for inferring disease similarity by similarity retrieval of electrocardiogram time-series, comprising: acquiring user ECG waveforms correspondingly depicting many cardiac cycles of the heart of many users stored in a database; pre-processing each of the user ECG waveforms through pre-processing steps to isolate sets of single cardiac cycles corresponding to different heart-rates detected for each of the user ECG waveforms, each single cardiac cycle within the many cardiac cycles of the heart of many users corresponds to one single heart-rate detected. acquiring patient ECG waveforms depicting multiple cardiac cycles of the heart of a query patient; pre-processing the patient ECG waveforms through pre-processing steps to isolate sets of single cardiac cycles corresponding to different heart-rates detected for each of the patient ECG waveforms of the query patient, each single cardiac cycle within the multiple cardiac cycles of the heart of the query patient corresponds to one single heart-rate detected.

4 Claims, 8 Drawing Sheets

OTHER PUBLICATIONS

Syeda-Mahmood, et al. "Finding Disease Similarity by Combining ECG with Heart Auscultation Sound" Computers in Cardiology, 2007; 24:261-264.*

Tuzcu, et al. "Dynamic Time Warping As a Novel Tool in Pattern Recognition of ECG Changes in Heart Rhythm Disturbances" IEE Intl Conference on Systems, Man and Cybernetics, 2005; 1:182-186.*

Huang, et al. "ECG frame classification using dynamic time warping" Proc. IEEE Canadian Conf. on Elec. and Comp. Engineering, 2005; 2:1105-1110.*

* cited by examiner

SYSTEM AND METHOD FOR INFERRING DISEASE SIMILARITY BY SHAPE MATCHING OF ECG TIME SERIES

BACKGROUND OF THE INVENTION

1. Field of the Invention

This invention relates generally to comparison of cardiac waveform and, more particularly, to a system and a method for searching for similar ECGs to infer similar diseases by a matching of the shape of ECG time series.

2. Description of Background

An electrocardiogram (EKG or ECG) is an electrical recording of the heart that depicts the cardiac cycle. It is routinely used as a first course of choice in diagnosing many cardiovascular diseases. Often, twelve electrodes are used to record the electrical activity of the heart from different viewpoints. A normal ECG waveform (in lead II) has a characteristic shape as illustrated in FIG. 1A. The segment labeled P represents the phase of atrial depolarization/contraction when the impure blood enters the heart from the left atrium and pure blood enters the heart from the lungs into the right atrium (FIG. 1B). The QRS segment represents the phase of ventricular depolarization/contraction when blood enters the left and right ventricles for ejecting into the pulmonary and aorta respectively. Finally, the T segment represents ventricular repolarization where the ventricles relax to allow the cycle to begin again. Many disturbances in the heart function show as characteristic variations in the sinus rhythm waveform of FIG. 1A and can be used as cues to diagnose the disease. FIG. 1C shows such a modification in the ECG due to premature ventricular contraction where the heart skips a beat only to beat very strongly in the next causing a missed R segment. Physicians routinely make diagnosis by a simple visual examination of these ECG waveforms. It is common knowledge to physicians that patients with the same disease have similar-looking ECG shape in the relevant channels (leads). Examples of such similarity can be seen in FIG. 2, which shows ECG recording of several patients all diagnosed with bundle branch block.

This observation of similarity, however, is after factoring out a number of morphological variations that can be attributed to heart rate variability, disease-specific variability, and measurement variability in ECG recordings that affect the amplitude levels. Further, there seems to be a built-in tolerance to disease-specific variability that often manifests as small relative translation of characteristic segments of the ECG such as the P, Q, R, S, and T while still preserving the shape of the segments.

There are a number of algorithms available for single ECG analysis, and for ECG classification based on neural network, expert and fuzzy expert systems, machine learning methods, wavelet transforms and genetic algorithms. The rule-based methods rely on the accuracy of the P-Q-R-S-T segment detection. Errors in estimation of these feature values can cause major errors in disease-specific interpretation. Further, in order to distinguish combinations of diseases, a finer shape analysis of the ECG waveform may be required. The parametric modeling methods, on the other hand, are good at spotting major disease differences but can't take into account fine morphological variability due to heart rate (e.g., ventricular vs. supra-ventricular tachycardia) and physiological differences.

Related work in the time alignment of ECGs also exists. Dynamic time warping (DTW) has been a popular technique in ECG frame classification, and more recently, in the recognition of heart beat patterns for synthetically generated signals. In all such alignments, however, the amplitude of the signal was used rather than a detailed modeling of the shape. Moreover, the DTW algorithm used did not explicitly model the morphological changes in the signal across patients with similar diseases, as it does not take into account missing and spurious fiducial features during alignment.

SUMMARY OF THE INVENTION

The shortcomings of the prior art are overcome and additional advantages are provided through the provision a method for inferring disease similarity by similarity retrieval of electrocardiogram time-series, the method comprising: acquiring a plurality of user ECG waveforms correspondingly depicting many cardiac cycles of the heart of many users stored in a database; pre-processing each of the plurality of user ECG waveforms through a first plurality of pre-processing steps to isolate sets of single cardiac cycles corresponding to different heart rates detected for each of the plurality of user ECG waveforms, each single cardiac cycle within the many cardiac cycles of the heart of many users corresponds to one single heart rate detected; acquiring one or more patient ECG waveforms depicting multiple cardiac cycles of the heart of a query patient; pre-processing the one or more patient ECG waveforms through a second plurality of pre-processing steps to isolate sets of single cardiac cycles corresponding to different heart rates detected for each of the one or more patient ECG waveforms of the query patient, each single cardiac cycle within the multiple cardiac cycles of the heart of the query patient corresponds to one single heart rate detected; and successively comparing each single cardiac cycle of the one or more patient ECG waveforms to each single cardiac cycle of the plurality of user ECG waveforms stored in the database based on a non-rigid shape matching technique that maximizes the match of the one or more patient ECG waveforms while allowing for gaps and insertions and choosing the best possible matching pair to infer disease labels.

Additional features and advantages are realized through the techniques of the present invention. Other embodiments and aspects of the invention are described in detail herein and are considered a part of the claimed invention. For a better understanding of the invention with advantages and features, refer to the description and to the drawings.

TECHNICAL EFFECTS

As a result of the summarized invention, technically we have achieved a solution for searching for similar ECGs to infer similar diseases by a matching of the shape of ECG time series.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

Figure 1A:
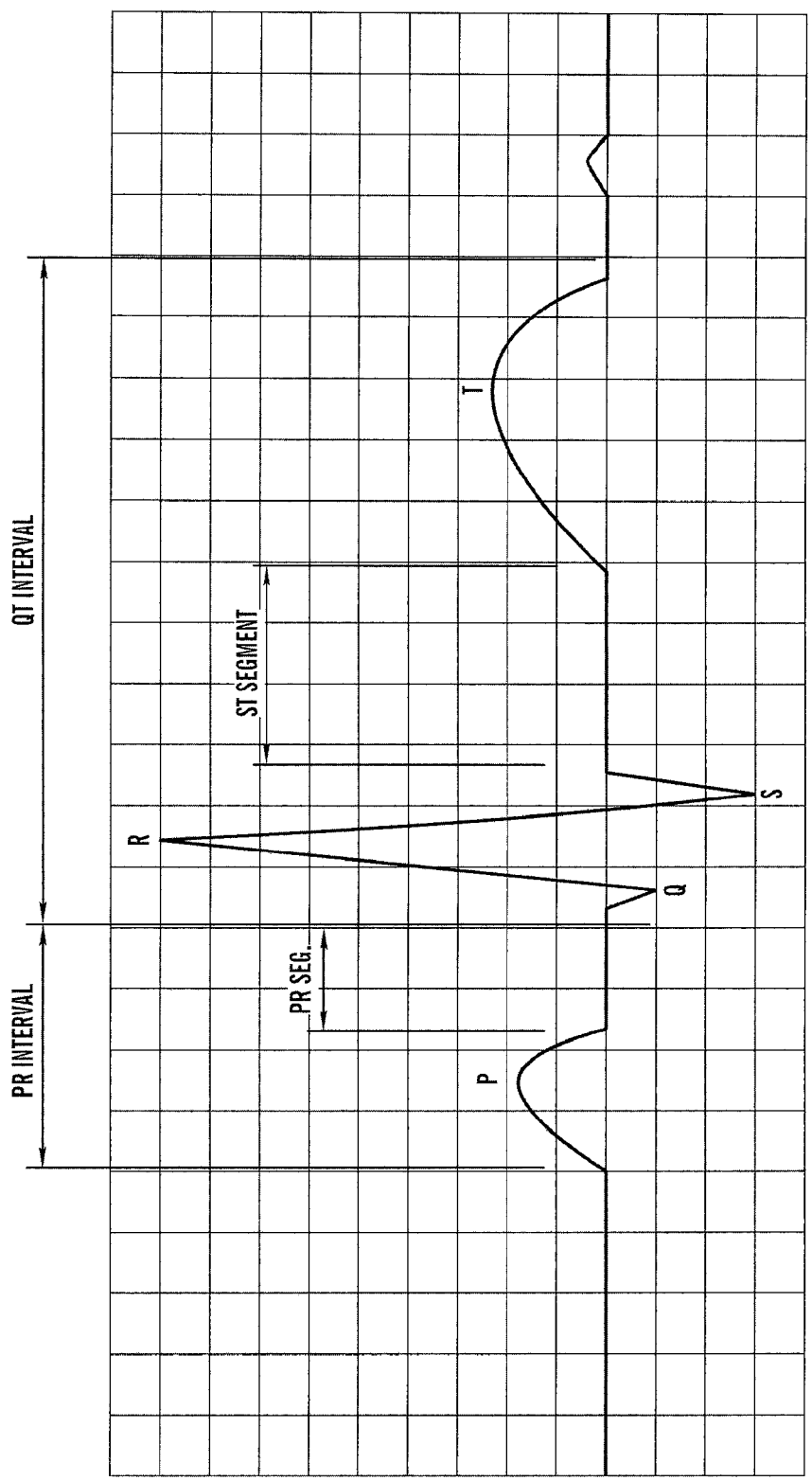
FIG. 1A illustrates a schematic of an exemplary heart cycle.

The detailed description explains the preferred embodiments of the invention, together with advantages and features, by way of example with reference to the drawings.

DETAILED DESCRIPTION OF THE INVENTION

The present invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known or conventional components and processing techniques are omitted so as to not necessarily obscure the present invention in detail. The examples used herein are intended merely to facilitate an understanding of ways in which the invention may be practiced and to further enable those of skill in the art to practice the invention. Accordingly, the examples should not be construed as limiting the scope of the invention.

For all general purposes, the electrical signals measured by an ECG are characterized and represent various phases of a heartbeat. The heart produces three distinct ECG waves. The first that is seen in the cycle is called the P wave, which measures the electrical signal generated by the pacemaker region of the heart. The next pulse is the largest signal, which is often referred to as the QRS complex. This segment of the ECG represents the electrical signal created by the relaxing of the atria and the contraction of the ventricles. The T wave completes the cycle. This wave signifies the relaxing or repolarization of the ventricles.

The inventors herein have recognized that perceptual similarity in the shape of ECGs, if automatically captured, can be used to infer the similarity of diseases among the ECGs, which can lead to automatic diagnosis validation systems. The inventors herein have recognized an approach that models shape matching as a problem of shape approximation under a constrained non-rigid transform, which is recovered using a variant of dynamic time warping that explicitly accounts for missing and spurious fiducial features in ECGs. Such approach can provide similarity comparison with ECGs previously captured. This will become more apparent with the description below.

Figure 3:
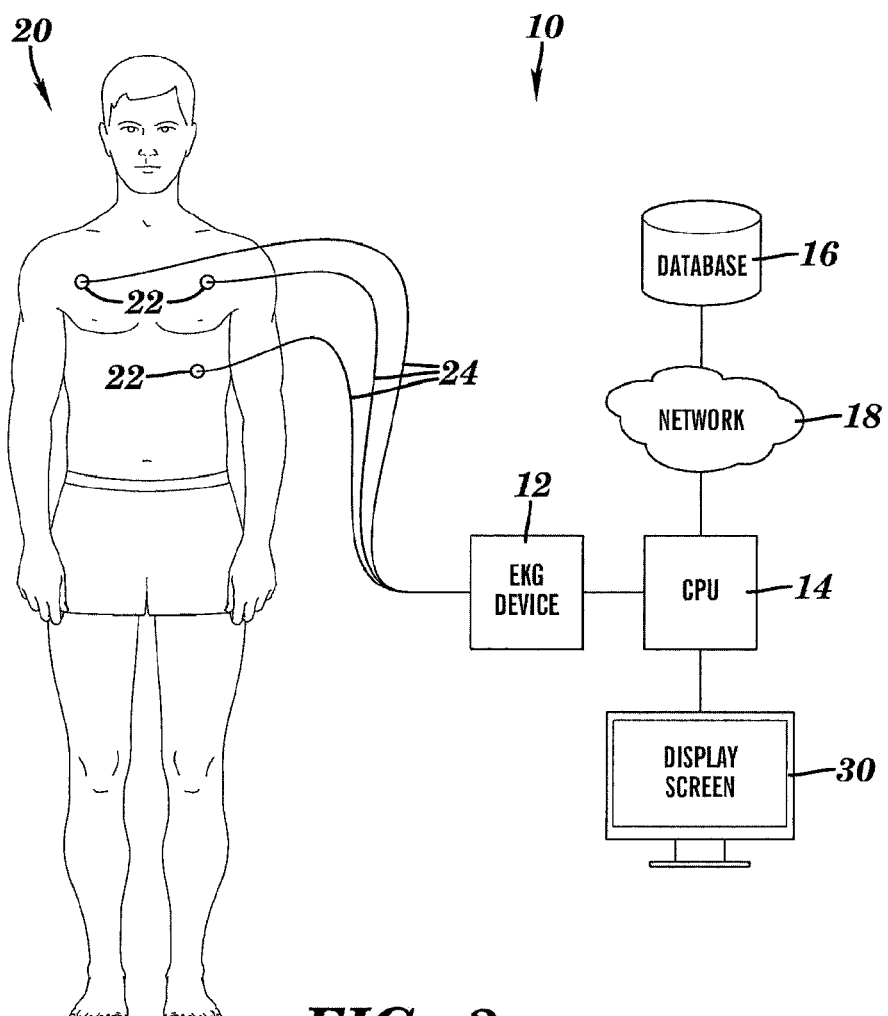
FIG. 3 illustrates a schematic of an automated electrocardiogram system in accordance with exemplary embodiments of the present invention.

For a better understanding of the invention and its operation, turning now to the drawings, FIG. 3 is a simplified schematic illustrating the basic elements of an automated ECG system 10 in accordance with exemplary embodiments of the present invention. The automated system 10 includes an ECG device 12, a central processing unit (CPU) 14, and a database 16 in signal communication with the CPU 14 via a network 18 in accordance with one exemplary embodiment.

The ECG device 12 may be any conventional ECG machine or device configured for measuring or recording the electrical activity of the muscles of the heart of a user 20 in a relevant channel, which may vary depending on the application. In accordance with one embodiment, the ECG device 12 includes electrodes or leads 22 coupled to connecting wires 24. The electrodes 20 are configured for being disposed on various sections of the user (e.g., left chest) for measuring the electrical pulses or activity of the heart of the user. The ECG device 12 produces an ECG waveform or signal or ECG time series of the user, hereinafter referred to as user ECG waveform, depicting a cardiac cycle of the user. In accordance with one embodiment, the user ECG waveform depicts the cardiac cycle of the user over a period of time or during a number of heartbeats.

The CPU 14 operably communicates with ECG device 12 and database 16 in real-time in accordance with one embodiment. In accordance with one exemplary embodiment, the CPU 14 may be any conventional processor configured for carrying out the methods and/or functions described herein. In one exemplary embodiment, the CPU 12 comprises a combination of hardware and/or software/firmware with a computer program that, when loaded and executed, permits the CPU 12 to operate such that it carries out the methods described herein. In one embodiment, the CPU 12 is an integral part of the ECG device 12 as shown in FIG. 3 or is separate from the same in accordance with another embodiment. In either configuration, the CPU 12 is configured for receiving the user ECG waveform measured by the ECG device 12 and modeling the same to obtain disease-specific conclusions from other ECGs.

Computer program means or computer program used in the present context of exemplary embodiments of the present invention include any expression, in any language, code, notation, or the like of a set of instructions intended to cause a system having information processing capabilities to perform a particular function either directly or after conversion to another language, code, notation, or the like reproduction in a different material form.

In accordance with one exemplary embodiment, the CPU 12 is in signal communication with database 16 via the network 18. The database 16 may be any conventional storage device for storing data in accordance with one embodiment. In one exemplary embodiment, the data stored in database 16 comprises a broad range of ECG waveforms of other users having one or more diseases associated therewith that have been obtained in a particular channel(s). For example, the ECG waveform of user 0006 in the database has been diagnosed with disease X, Y, and Z, which are indicative of a particular disease affecting the heart (e.g., Bradycardia).

In accordance with one embodiment, the CPU 12 captures the shape of the user ECG waveform acquired by the ECG device 12 and models the shape of the ECGs in the database such that a comparison between the user ECG waveform and each of the ECG waveforms stored in the database 16 can be performed by the CPU 12 using a shape approximation technique under a constrained non-rigid transform. Consequently, one or more diseases associated with the user ECG waveform can be inferred based on the comparison and the diseases associated with the other ECG waveforms stored in the database 16.

Figure 1B:
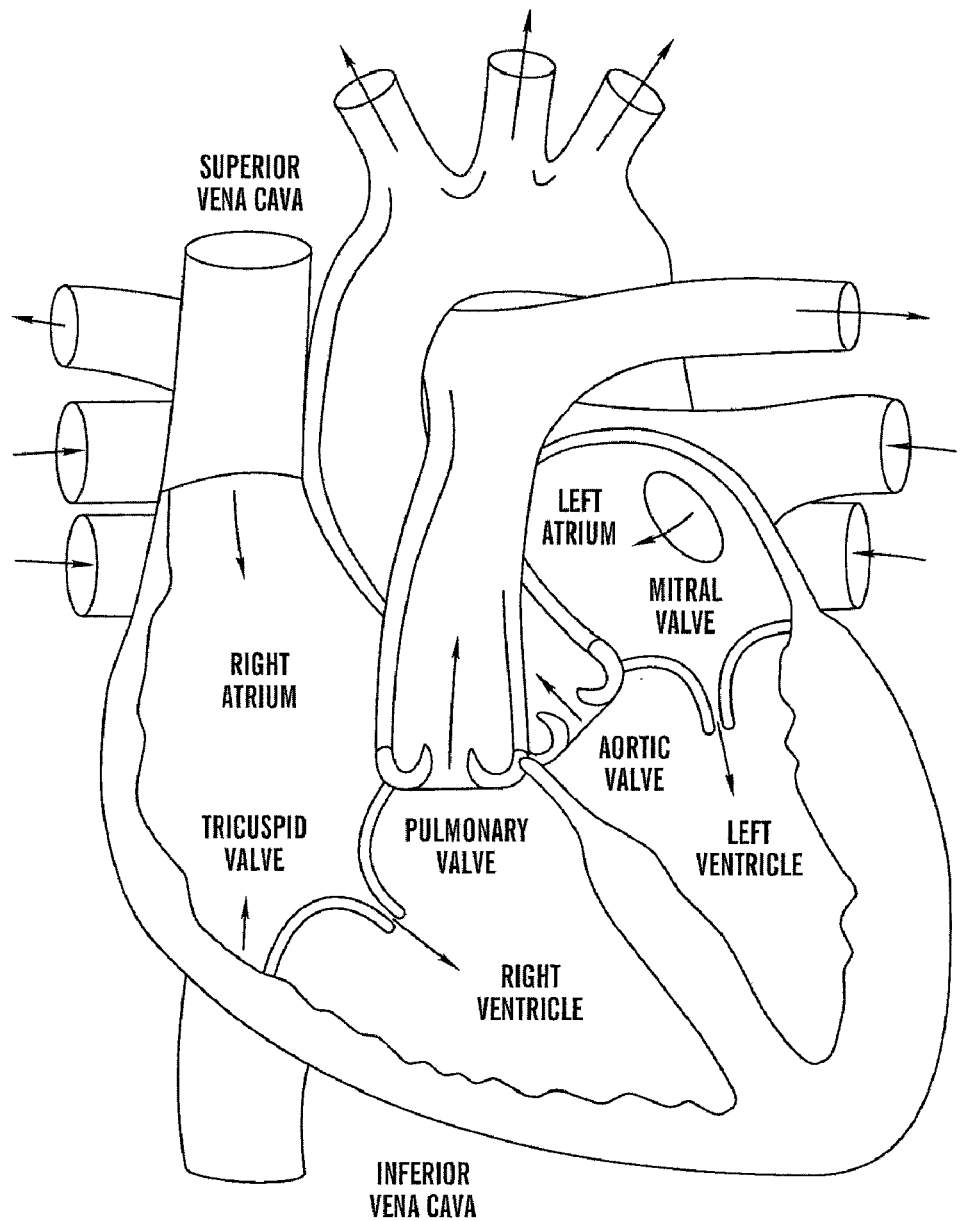
FIG. 1B illustrates a schematic of a normal electrocardiogram.
Figure 1C:
FIG. 1C illustrates a schematic of an abnormal electrocardiogram showing premature ventricular contraction.
Figure 2:
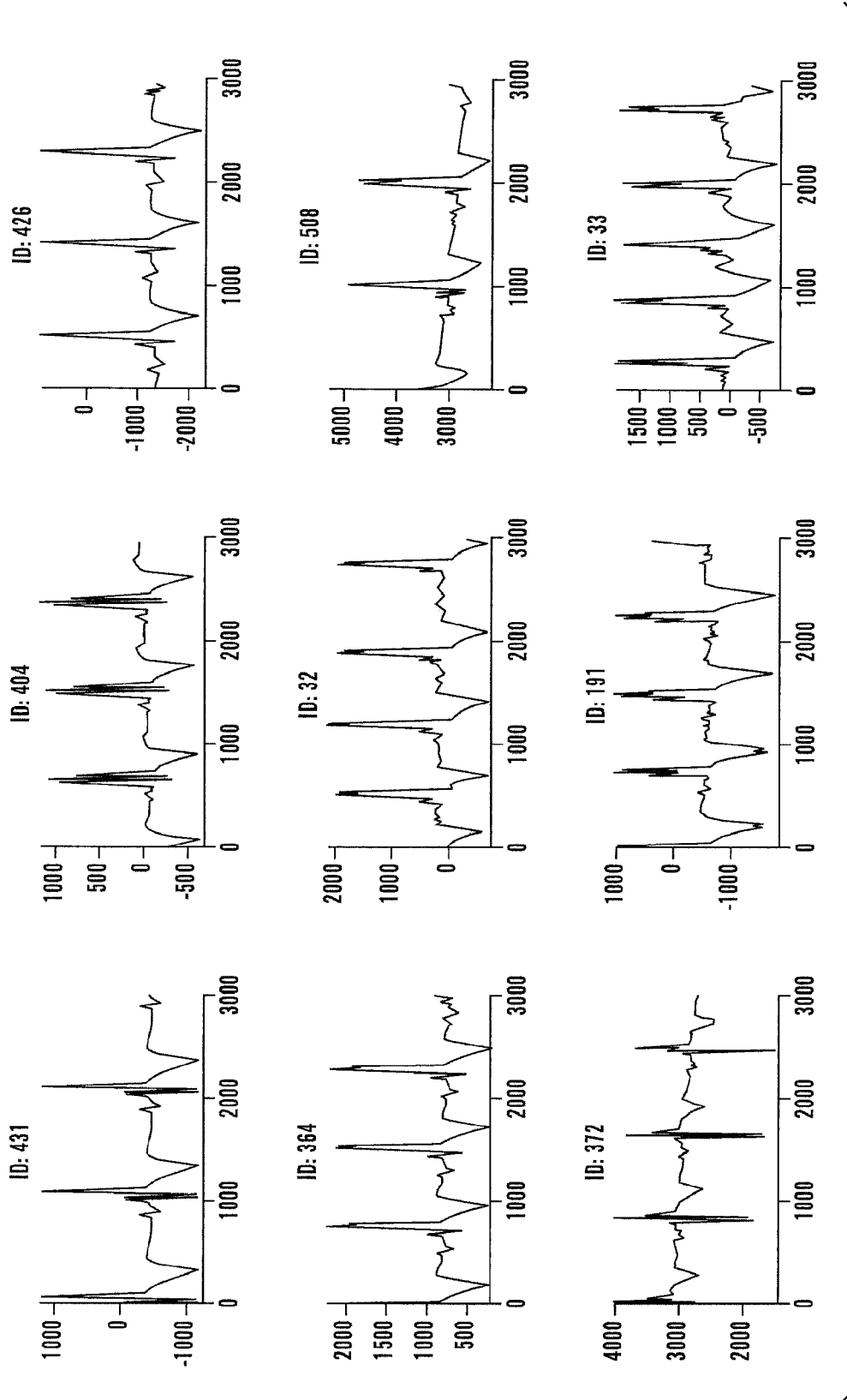
FIG. 2 illustrates a schematic of an electrocardiogram recording of several patients all diagnosed with Bundle Branch Block.

In accordance with one embodiment, the CPU 12 determines which of the ECG waveforms stored in the database 16 are the best matches to the user ECG waveform. The CPU 12 determines the best matches by selecting the ECG waveforms with the greatest amount of similarities in shape or aligns the best with the user ECG waveform in accordance with one embodiment. The ECG waveforms with the greatest amount of similarities in shape with the user ECG waveform are displayed in a display screen 30 (FIG. 1) in accordance with one exemplary embodiment. Furthermore, the distribution of diseases associated with the ECG waveforms selected and stored in the database 16 can be displayed in a statistical report in accordance with other exemplary embodiments of the present invention. In other words, labels (type or name) of the diseases from the other ECG waveforms that closely match with the user ECG waveform based on the comparison can be recovered and a graph displaying a distribution of labels as a statistical reported based on the matching can be generated and displayed via the display screen 30. It is contemplated that other information relating to the ECG waveform and the user of the same can be displayed via the display screen 30. Other information may include, but should not be limited to, ethnicity of the user, other non-heart related issues, weight, diet, treatment, etc.

In operation, the ECG device 12 acquires the user ECG waveform via the electrodes 22 disposed on the user. The CPU 12 then automatically captures the shape of the user ECG waveform and performs shape approximation technique under a constrained non-rigid alignment transform on the ECGs by modeling the shape variations of the ECGs. In this technique, the non-rigid alignment transform is recovered using a variant of dynamic time warping that explicitly accounts for missing and spurious fiducial features in the ECGs. Due to the periodic nature of ECGs, the duration of the user ECG waveform and the stored ECG waveforms considered for shape matching is restricted to a single heartbeat in accordance with one exemplary embodiment. Moreover, shape matching is restricted to similar channels.

A more detailed discussion of modeling the shape variations of ECGs performed by the CPU 12 will now be presented. Specifically, the algorithm in which the CPU 12 implements when modeling the shape variations of ECGs will be discussed by way of example. The algorithm begins by modeling the shape variations in ECGs taken from patients diagnosed with the same disease. For example, consider an ECG g(t) (time series) corresponding to disease X. For ease of discussion, assume that the relevant channel for the diagnosis of disease X is pre-selected. Consider another ECG f(t) (another time series) that is a potential match to g(t) corresponding to the same channel. The signal f(t) is considered perceptually similar to g(t) if a non-rigid transformed characterized by [a,b,Γ] can be found such that:

$$|f'(t)-g(t)| \leq \delta \qquad (1)$$

where || found in equation 1 represents the distance metric that measures the difference between f(t) and g(t), the simplest being the Euclidean norm. The function f'(t) can be expressed as:

$$f'(t)=af(\Phi(t)) \text{ with } \Phi(t)=bt+\Gamma(t) \qquad (2)$$

where (af) is the linear or uniform component of the transform and Γ is the non-linear or non-uniform translation component. As such, modeling shape variations includes a linear component translation and a non-linear component translation. The parameters a and b are solved by normalizing in amplitude and time. That is, f(t) and g(t) are transformed such that $$\hat{f}(t) = \frac{f(t) - f_{min}(t)}{f_{max}(t) - f_{minf}(t)} \text{ and } \hat{g}(t) = \frac{g(t) - g_{min}(t)}{g_{max}(t) - g_{minf}(t)} \qquad (3)$$

Consequently, a=1. Solving for b is eliminated by normalizing the time axis such that all time instants lie in the range [0,1]. Since the duration being considered is a single heart beat long, the time normalization is easily achieved by the following:

$$\vec{f}(t) = \hat{f}\left(\frac{t}{T_1}\right) \text{ and } \vec{g}(t) = \hat{g}\left(\frac{t}{T_2}\right) \qquad (4)$$

where $T_1$ and $T_2$ are the heart beat durations of f(t) and g(t) respectively. With this time normalization, b=1. Such amplitude and time normalization automatically make the shape modeling invariant to voltage variations in ECG recordings as well as variations in heart rate.

The non-linear translation Γ is a function of (t). The non-linear translation Γ is recovered at important fiducial point or features in the normalized signals. The overall shape approximation is recovered through time interpolation. For instance, let there be K features extracted from $\vec{f}(t)$ as $F_k=\{(t_1), \vec{f}_1(t_1)), (t_2), \vec{f}_2(t_2)), \ldots (t_k), \vec{f}_k(t_k))\}$ at time $\{t_1, t_2, t_k\}$ respectively. Furthermore, let there be M fiducial points (features) extracted from $\vec{g}(t)$ as $G_m\{(t'_1), \vec{g}_1(t'_1)), (t'_2), \vec{g}_2(t'_2)), \ldots (t'_m), \vec{g}_m(t'_m))\}$ at time $\{t'_1, t'_2, t'_m\}$ respectively. If a set of N matching fiducial points $C_\Gamma=\{(t_i, t'_j)\}$, then the non-uniform translation Γ can be defined as:

$$\Gamma(t') = \begin{cases} t_i & \text{if } t = t'_j \text{ and } (t_i, t'_j) \in C_\Gamma \\ t_r + \left(\frac{t_s - t_r}{t'_l - t'_k}\right)(t' - t'_k) & \text{where } (t_r, t'_k), (t_s, t'_l) \in C_\Gamma \end{cases} \qquad (5)$$

and $t_k$ is the highest of $\{t'_j\} \leq t'$ and $t'_l$ is the lowest of $\{t'_j\} \geq t'$ that have a valid mapping in $C_\Gamma$. It is contemplated that other interpolation methods besides linear (e.g., spline) may be used and should not be limited to the method described above.

Using equations 1 and 5, a shape approximation error between the two time series (f(t) and g(t)) is characterized by:

$$|f'(t)-g(t)|=|f(t')-\Gamma(t'))-g(t')| \qquad (6)$$

For each g(t), Γ is selected such that the same minimizes the approximation error in equation 6 while maximizing the size of $C_\Gamma$.

Determining the best matching ECG based on shape is formulated as finding the g(t) such that $$g_{best} = \arg\min |\vec{f}(\Gamma(t')) - g(t')| \quad (7)$$

while choosing the best $\Gamma$ for each respective candidate match g(t).

Now solving for $\Gamma$, the feature set $F_k$, $G_m$ extracted from the respective time series as sequences is considered. Computing for the best $\Gamma$ reduces to finding the best global subsequence alignment using the dynamic programming principle or a variant of DTW. The best global subsequence alignment maximizes the match of the time series fragments while allowing for possible gaps and insertions. Gaps and insertions correspond to signal fragments from feature sets $F_k$ that do not find a match in set $G_m$ and vice versa. In accordance with one embodiment, the alignment is computed using a dynamic programming matrix H where the element H(i,j) is the cost of matching up to the ith and jth element in the respective sequences. As more features find a match, it is desired that the cost increase as little as possible. The dynamic programming step in this example is characterized as:

$$H_{i,j} = \min \begin{cases} H_{i-1,j-1} + d(\vec{f}(t_i), \vec{g}(t'_j)) \\ H_{i-1,j} + d(\vec{f}(t_i), 0) \\ H_{i,j-1} + d(0, \vec{g}(t'_j)) \end{cases} \quad (8)$$

Figure 4:
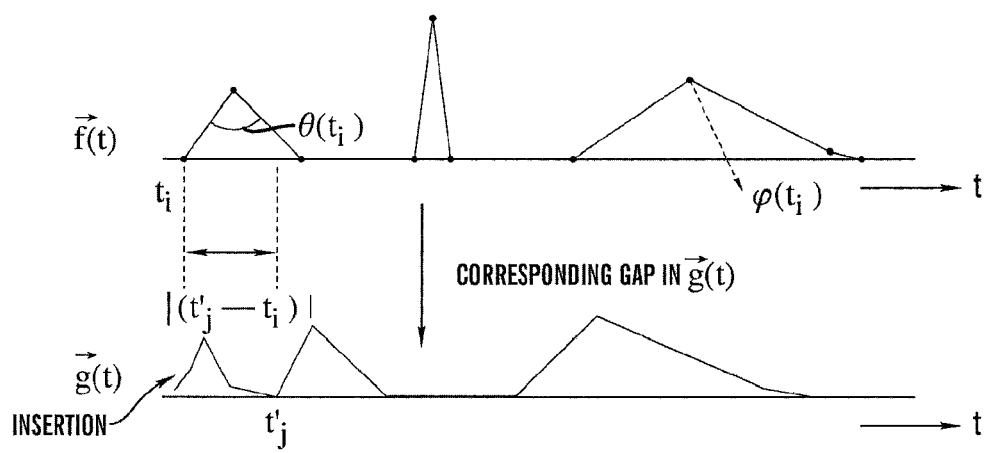
FIG. 4 is an exemplary diagram illustrating insertions and gaps being accounted for during the computation of the match between the two time series in accordance with exemplary embodiments of the present invention.

With initialization as $H_{0,0}=0$ and $H_{0,j}=\infty$ and $H_{i,0}=\infty$ for all $0<I\leq K$, and $0<j<M$. Here d( ) is the cost of matching the individual features, which will be described in more detail below. Also, the first term represents the cost of matching the feature point $\vec{f}(t_i)$ to feature point $\vec{g}(t'_j)$, which is low if the features are similar. The second term represents the choice where no match is assigned to feature $\vec{f}(t_i)$. The third term represents the case where there is not match to feature $g(t_j)$. FIG. 4 illustrates an exemplary diagram illustrating insertions and gaps being accounted for during the computation of the match between the two time series. Parameters extracted from fiducial feature are also shown in FIG. 4.

The time series can be regarded as curves where the fiducial points are the corners as shown in FIG. 4. The corners are obtained as the end point of a line segment approximation to curve. Other methods for extracting corners can be used without restricting the current invention. The shape information at each corner is modeled using the following parameters:

$$S(\vec{f}(t_i)) = <t_i, \vec{f}(t_i), \theta(t_i), \phi(t_i)> \quad (9)$$

where $\theta(t_i)$ is the included angle in the corner at $t_i$, and $\phi(t_i)$ is the orientation of the bisector at corner $t_i$. Using the angle of the corner ensures that wider QRS complexes are not matches to narrow QRS complex as these can change the disease interpretation. The angular bisector, on the other hand, ensures that polarity reversals such as inverted T waves or change in ST elevation can be captured. It is assumed that $(\theta(t_i), \phi(t_i))$ are both normalized to lie in the range [0,1] as are $t_i$ and $\vec{f}(t_i)$. The fiducial points in $\vec{g}(t)$ can be defined similarly. The cost function $d(\vec{f}(t_i), \vec{g}(t'_j))$ is given as the Euclidean distance between the two fiducial points using the following four parameters as:

$$d(\vec{f}(t_i), \vec{g}(t'_j)) = \begin{cases} \sqrt{\begin{array}{c}(t_i - t'_j)^2 + (\vec{f}(t_i) - \vec{g}(t'_j))^2 \\ (\theta(t_i) - \theta(t'_j))^2 + (\phi(t_i) - \phi(t'_j))^2\end{array}} \\ \infty \quad \text{otherwise} \end{cases} \quad (11)$$

if $$|(t_i - t'_j)| \leq \lambda_1$$
$$|(\vec{f}(t_i) - \vec{g}(t'_j))| \leq \lambda_2$$
$$|(\theta(t_i) - \theta(t'_j))| \leq \lambda_3$$
$$|(\phi(t_i) - \phi(t'_j))| \leq \lambda_3$$

The thresholds ($\lambda_1, \lambda_2, \lambda_3, \lambda_4$,) are predetermined thresholds based on expected variations between diseases. The cost function $d(\vec{f}(t_i))$ is computed by substituting $t'_j=0$, $\vec{g}(t'_j)=0$, and $\theta(t'_j)=0$, $\phi(t'_j)=0$ in Equation 11. The cost function $d(\vec{g}(t_i))$ is similarly computed. It is to be noted that the above formalism easily admits other information about fiducial features, including features that measure the axis of the heart using the difference in positive and negative deflections of the ECG wave.

Figure 5A:
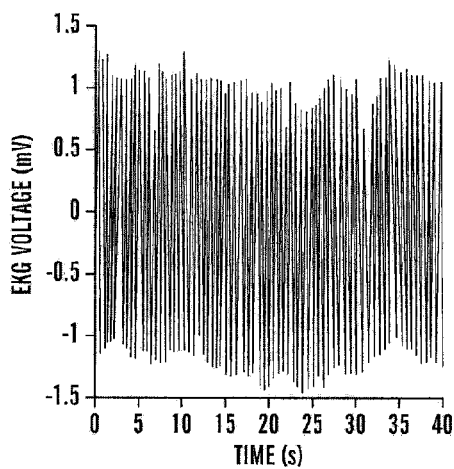
FIG. 5a illustrates a raw electrocardiogram signal in accordance with exemplary embodiments of the present invention.
Figure 5B:
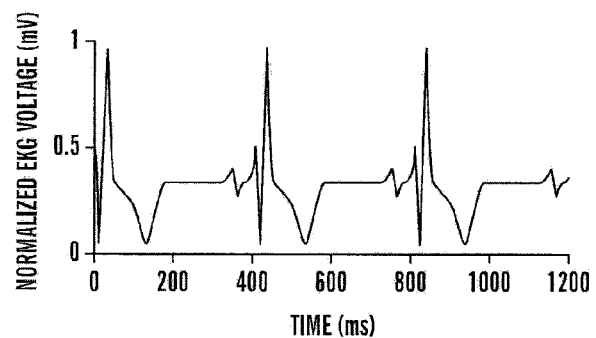
FIG. 5b illustrates a segment of the raw electrocardiogram signal in FIG. 3A in accordance with exemplary embodiments of the present invention.
Figure 5C:
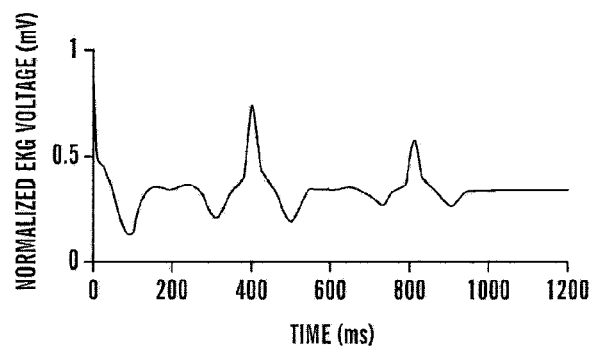
FIG. 5c illustrates detection of periodicities in the raw electrocardiogram signal by autocorrelation function in accordance with exemplary embodiments of the present invention.
Figure 5D:
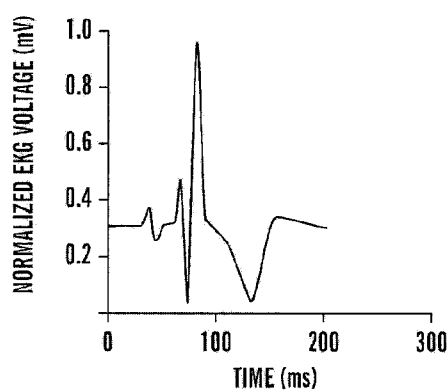
FIG. 5d illustrates a single period of the raw electrocardiogram signal automatically extracted from the raw electrocardiogram signal in accordance with exemplary embodiments of the present invention.

The overall shape-matching algorithm to align a pair of ECG signals or waveforms taken from the same observation channel consists of several steps and will now be discussed in reference to the steps and equations described in above. Generally, the algorithm consists of pre-processing steps and shape matching steps, which will be described in more detail below. While noise in a channel is seen in some heart beat cycles, the baseline wandering is a frequency noise distortion seen over the course of the entire signal as illustrated in an exemplary diagram in FIG. 5a. Some of the noise is removed during the line segment approximation as described above. To minimize the baseline-wandering problem, segments that are approximately 3000 samples long are selected to correspond to the usual three-second observations used in conventional ECG visual interpretations. Of course, the sampling cycle and the observation time may vary and should not be limited to the example described above. Such sampling and observation time ensures that a single heart beat interval is captured even in cases of severe Bradycardia. An exemplary diagram in FIG. 5b illustrates a segment of the raw signal of FIG. 5a where the baseline wandering effect is minimal. Next, to extract the single heart beat duration, signal f(t) is normalized in amplitude as given in Equation 3 and the autocorrelation function is computed. As shown in an exemplary diagram in FIG. 5c, the peaks in the autocorrelation function correspond to the various periodicity patterns found in the signal. The most common inter-peak duration is representative of a heart beat duration. Then, extract a segment of recovered duration from the ECG signal. This segment becomes the basis of the shape-based alignment scheme. The signal heartbeat-containing region extracted using the inter-peak distance in the autocorrelation function of FIG. 5c is shown in an exemplary diagram in FIG. 5d.

The normalization of the time axis for a single heart beat duration is performed as given by Equation 4. This ensures that all signals being compared are one heart beat long and have their time values ranges from 0-1.

Figure 5E:
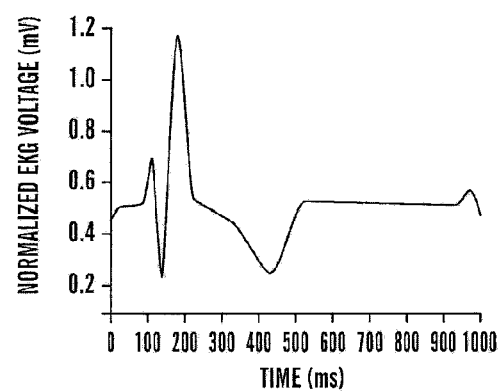
FIG. 5e is an exemplary graph illustrating fiducial points extracted using a line segment curve approximation for the signal in FIG. 3d in accordance with exemplary embodiments of the present invention.

The fiducial points extracted from the time series are corners. A simple line segment approximation that does a recursive partitioning of the time series curved can be used. In this scheme, the points along the curve are successively merged into lines if their deviation from a candidate line is within the threshold. The candidate line is chosen starting from joining the end points and finding the point of highest deviation from the line as the next point to split the curve. In one example, a threshold on minimum length=5, and amplitude deviation of 0.01 is sufficient to remove much of the noise wile still keeping the main P, Q, R, S, T features. FIG. 5e is an exemplary diagram illustrating the fiducial points extracted using the line segment curve approximation for the signal shown in FIG. 5d.

By selecting one heart beat interval from the original signal, there is an initial translation bias depending on the starting point for such selected interval. The signals as a result may need to be circularly shifted to perform an initial registration. As the translation required is usually much larger than that is allowed during DTW alignment, it is extracted separately. As such, the two signals to be matches are cross-correlated. The translation corresponds to the peak as the initial translation. Since the signals are periodic, a circular shift is performed. Once the signals are initially registered, the DTW alignment is performed as previously described. The alignment transform is then used to project one signal onto the other as given in Equation 5 and the residual error is evaluated using equation 6.

Figure 6A:
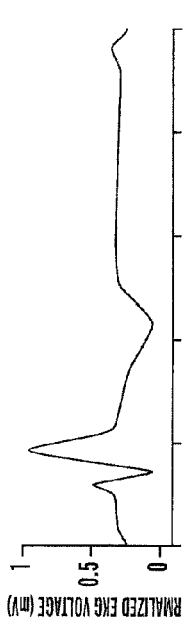
FIGS. 6a-6h are exemplary graphs illustrating the shape-matching algorithm in accordance with exemplary embodiments of the present invention.
Figure 6B:
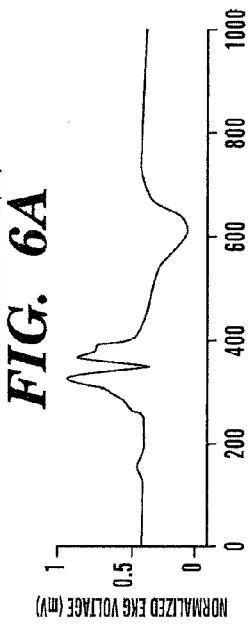
Figure 6C:
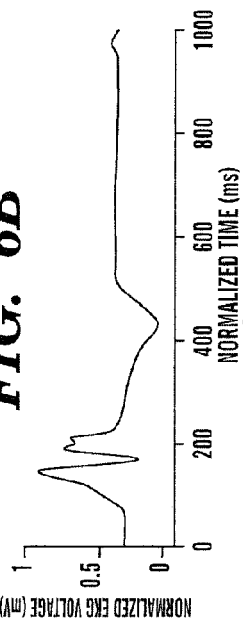
Figure 6D:
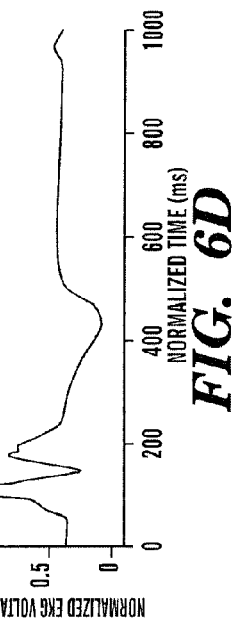
Figure 6E:
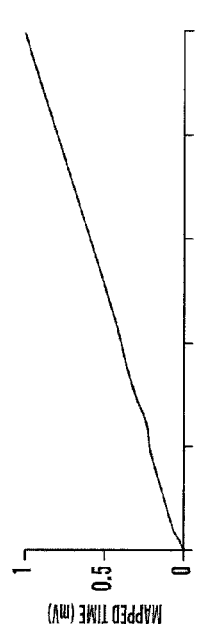
Figure 6F:
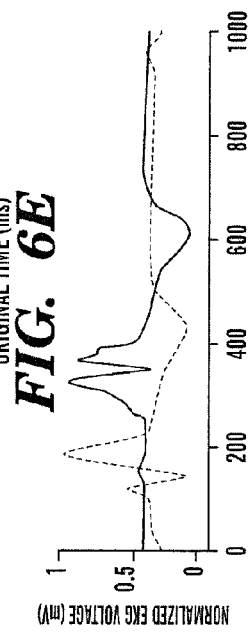
Figure 6G:
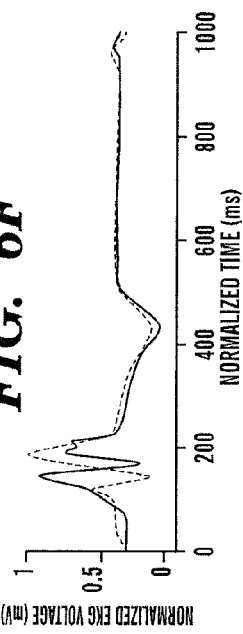
Figure 6H:
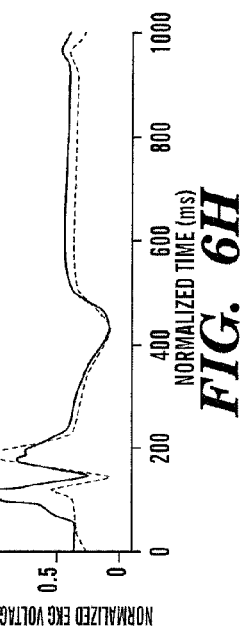

Now referring to FIGS. 6a-6h, exemplary graphs are provided illustrating the shape-matching algorithm. The candidate ECG to be matched after the pre-processing step is shown in FIGS. 6a and 6b. The result of initial alignment using cross-correlation is shown in FIG. 6c. FIG. 6d illustrates the result of shape alignment using DTW for the signal in FIG. 6b. Comparing the simple overlaid shapes of FIG. 6f with FIG. 6h shows the improvement in shape matching due to non-rigid DTW alignment. The alignment itself is illustrated in FIG. 6e. As can be seen, the alignment is close to the diagonal illustrating a good match.

This pair-wise matching of single heart beat intervals is repeated over multiple heartbeat segments over the available data and the average residual error is used to rank the matches.

In sum, the key steps of the overall shape-matching algorithm includes pre-processing steps, which comprises of the pre-processing of each ECG waveform stored in the database to reduce the effect of baseline wandering by dividing the ECG into small segments containing one or two cycles. The pre-processing steps further comprises of isolating a single heart beat cycles using the autocorrelation function on the ECG time series in the respective channels. The pre-processing steps further comprises of normalizing the amplitude and time of the signal so that all features are expressed as a percentage distance from the end of a heart beat duration. This makes the matching time and signal amplitude invariant. The pre-processing steps further comprise treating ECG waveform as a curve, extracting corners, and noting their location, angle, and the orientation of the bisector.

The key steps of the overall shape-matching algorithm further includes shape matching steps of the user ECG waveform, which comprises pre-processing the user ECG waveform as described above. The shape matching steps of the user ECG waveform further comprises performing an initial alignment of the user ECG waveform with one of the ECG waveforms stored in the database by cross-correlating the two waveforms. The shape matching steps of the user ECG waveform further comprises performing a detailed alignment by using shape-based dynamic time warping. The shape-based constraints used will be based on the attributes of the corners extracted (i.e., distance between features based on their location, angle of corner, and orientation of the bisector). Of course, other feature attributes can be used and should not be limited to the attributes described above. The shape matching steps of the user ECG waveform further comprises ranking the matches by combining the alignment scores. In accordance with one exemplary embodiment, the EKG device 12 generates a list of one or more of the plurality of ECG waveforms that closely matches with the patient ECG waveform based on the comparison in a descending order of similarity via the display screen 30.

Figure 7:
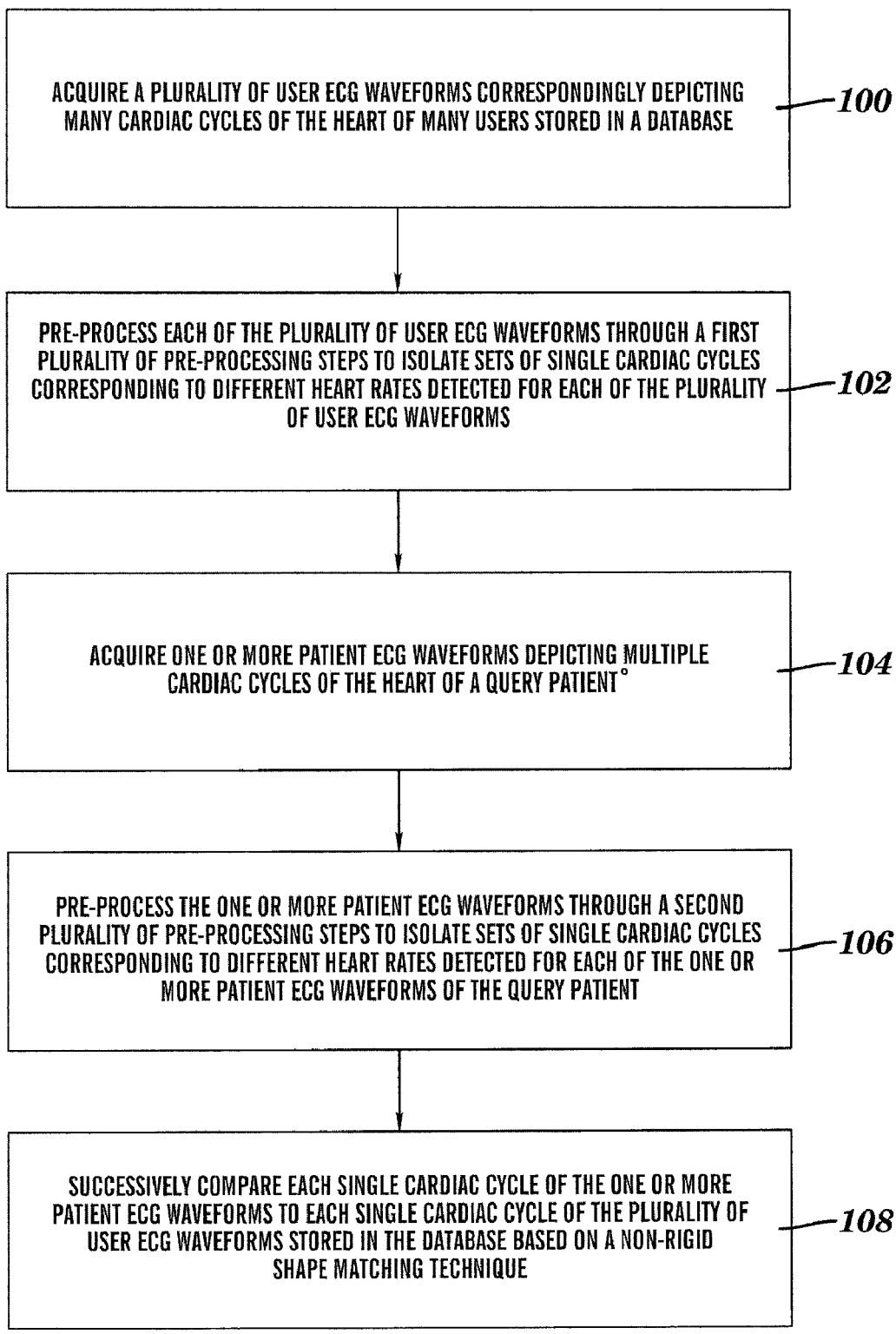
FIG. 7 is a flow diagram illustrating a method for searching for similar ECGs to infer similar diseases by a matching of the shape of ECG time series in accordance with exemplary embodiments of the present invention.

In accordance with an exemplary embodiment of the present invention, an exemplary method for inferring disease similarity by shape matching electrocardiogram time series is provided and illustrated in FIG. 7. In this exemplary method, acquire a plurality of user ECG waveforms correspondingly depicting many cardiac cycles of the heart of many users stored in a database in block 100. Next, pre-process each of the plurality of user ECG waveforms through a first plurality of pre-processing steps to isolate sets of single cardiac cycles corresponding to different heart rates detected for each of the plurality of user ECG waveforms in block 102. In accordance with one exemplary embodiment, each single cardiac cycle within the many cardiac cycles of the heart of many users corresponds to one single heart rate detected. In accordance with one exemplary embodiment, the first plurality of pre-processing steps include obtaining the plurality of user ECG waveforms through multiple channels and removing the noise in each of the plurality of user ECG waveforms without losing significant signal changes. The first plurality of pre-processing steps further include segmenting the plurality of user ECG waveforms into single cardiac cycles and determining the corresponding heart rates detected in each of the plurality of user ECG waveforms in accordance with one exemplary embodiment. The first plurality of pre-processing steps even further include extracting a first plurality of fiducial shape features from each cardiac cycle isolated from the plurality of user ECG waveforms and extracting a first plurality of shape properties from the first plurality of fiducial features and storing the first plurality of shape properties in the database in accordance with one exemplary embodiment. Then, acquire one or more patient ECG waveforms depicting multiple cardiac cycles of the heart of a query patient in block 104. In block 106, pre-process the one or more patient ECG waveforms through a second plurality of pre-processing steps to isolate sets of single cardiac cycles corresponding to different heart rates detected for each of the one or more patient ECG waveforms of the query patient. In accordance with one exemplary embodiment, each single cardiac cycle within the multiple cardiac cycles of the heart of the query patient corresponds to one single heart rate detected. In accordance with one exemplary embodiment, the second plurality of pre-processing steps include obtaining the one or more patient ECG waveforms through multiple channels and removing the noise in the one or more patient ECG waveforms without losing significant signal changes. The second plurality of pre-processing steps further include segmenting the one or more patient ECG waveforms into single cardiac cycles and determining the corresponding heart rates detected in the one or more patient ECG waveforms in accordance with one exemplary embodiment. The second plurality of pre-processing steps even further include extracting a second plurality of fiducial shape features from the one or more patient ECG waveforms and extracting a second plurality of shape properties from the second plurality of fiducial shape features. In block 108, successively compare each single cardiac cycle of the one or more patient ECG waveforms to each single cardiac cycle of the plurality of user ECG waveforms stored in the database based on a non-rigid shape matching technique. In one exemplary embodiment, the non-rigid shape matching technique as described above maximizes the match of the one or more patient ECG waveforms while allowing for gaps and insertions and choosing the best possible matching pair to infer disease labels. In accordance with one exemplary embodiment, the plurality of ECG waveforms correspondingly of other users are stored in the database of the automated electrocardiogram system and each of the plurality of ECG waveforms correspondingly of other users includes one or more of a plurality of diseases corresponding therewith.

It is contemplated that the automatic capture of perceptual shape similarity in ECG waveforms to infer similarity in disease can be performed on scanned printed ECGs as well as digital ECG recordings acquired by the ECG device 12.

Exemplary embodiments of the present invention provide a model developed to capture the disease-specific deviations in ECGs. In accordance with one exemplary embodiment, the database is grouped by diseases. Exemplary embodiments of the present invention intend to find similar shape time series in order to provide diagnosis reports that show the distribution of disease labels of the ECGs found to be similar. Furthermore, exemplary embodiments of the present invention provides short-time signal analysis by successively comparing single cardiac cycles as described above.

The flow diagrams depicted herein are just examples. There may be many variations to these diagrams or the steps (or operations) described therein without departing from the spirit of the invention. For instance, the steps may be performed in a differing order, or steps may be added, deleted or modified. All of these variations are considered a part of the claimed invention While the preferred embodiment to the invention has been described, it will be understood that those skilled in the art, both now and in the future, may make various improvements and enhancements which fall within the scope of the claims which follow. These claims should be construed to maintain the proper protection for the invention first described.

What is claimed is:

1. A method for inferring disease similarity by shape matching electrocardiogram (ECG) time series, the method comprising:

acquiring a plurality of user ECG waveforms correspondingly depicting many cardiac cycles of the heart of many users stored in a database;

pre-processing each of the plurality of user ECG waveforms through a first plurality of pre-processing steps to isolate sets of single cardiac cycles corresponding to different heart rates detected for each of the plurality of user ECG waveforms, each single cardiac cycle within the many cardiac cycles of the heart of many users corresponds to one single heart rate detected;

acquiring one or more patient ECG waveforms depicting multiple cardiac cycles of the heart of a query patient;

pre-processing the one or more patient ECG waveforms through a second plurality of pre-processing steps to isolate sets of single cardiac cycles corresponding to different heart rates detected for each of the one or more patient ECG waveforms of the query patient, each single cardiac cycle within the multiple cardiac cycles of the heart of the query patient corresponds to one single heart rate detected; and successively comparing each single cardiac cycle of the one or more patient ECG waveforms to each single cardiac cycle of the plurality of user ECG waveforms stored in the database based on a non-rigid shape matching technique that maximizes the match of the one or more patient ECG waveforms while allowing for gaps and insertions labels; and further comprising: recovering disease labels of one or more of the plurality of diseases from one or more of the plurality of user ECG waveforms that closely matches with the patient ECG waveform based on the comparison; and generating a graph displaying a distribution of labels as a statistical report based on the matching.

2. The method as in claim 1, wherein the first plurality of pre-processing steps comprises:

obtaining the plurality of user ECG waveforms through multiple channels;

removing the noise in each of the plurality of user ECG waveforms without losing significant signal changes;

segmenting the plurality of user ECG waveforms into single cardiac cycles and determining the corresponding heart rates detected in each of the plurality of user ECG waveforms;

extracting a first plurality of fiducial shape features from each cardiac cycle isolated from the plurality of user ECG waveforms; and extracting a first plurality of shape properties from the first plurality of fiducial features and storing the first plurality of shape properties in the database.

3. The method as in claim 1, wherein the second plurality of pre-processing steps comprises:

obtaining the one or more patient ECG waveforms through multiple channels;

removing the noise in the one or more patient ECG waveforms without losing significant signal changes;

segmenting the one or more patient ECG waveforms into single cardiac cycles and determining the corresponding heart rates detected in the one or more patient ECG waveforms;

extracting a second plurality of fiducial shape features from the one or more patient ECG waveforms; and extracting a second plurality of shape properties from the second plurality of fiducial shape features.

4. The method as in claim 1, further generating a list of one or more of the plurality of user ECG waveforms that closely matches with the patient ECG waveform based on the comparison in a descending order of similarity.

* * * * *